United States Patent [19]

Farooq et al.

[11] 4,072,752
[45] Feb. 7, 1978

[54] PESTICIDAL BENZASPIRO CARBOXYLATES

[75] Inventors: Saleem Farooq, Aesch; Jozef Drabek, Allschwil; Laurenz Gsell, Fullinsdorf; Friedrich Karrer, Zofingen; Willy Meyer, Riehen, all of Switzerland

[73] Assignee: Ciba-Geigy Corporation, Ardsley, N.Y.

[21] Appl. No.: 724,141

[22] Filed: Sept. 17, 1976

[30] Foreign Application Priority Data

Sept. 26, 1975  Switzerland .................. 12566/75
July 29, 1976   Switzerland .................. 9736/76
Apr. 29, 1976   Switzerland .................. 5388/76

[51] Int. Cl.$^2$ .................. A01N 9/20; A01N 9/24; C07C 121/66; C07C 69/76
[52] U.S. Cl. .................. 424/304; 260/465 D; 424/308; 560/8
[58] Field of Search .................. 260/465 D, 469; 424/304, 308

[56] References Cited
U.S. PATENT DOCUMENTS

| | | | |
|---|---|---|---|
| 3,786,052 | 1/1974 | Martel | 260/240 R |
| 3,962,458 | 6/1976 | Schrider | 424/304 |
| 3,979,519 | 9/1976 | Punja | 424/304 |

*Primary Examiner*—Dolph H. Torrence
*Attorney, Agent, or Firm*—Harry Falber

[57] ABSTRACT

2,2-Dimethyl-4,5-benzospiro(2,4)heptane- and 2,2-dimethyl-4,5-benzospiro(2,4)-hepta-4,6-diene-1-carboxylates of the formula

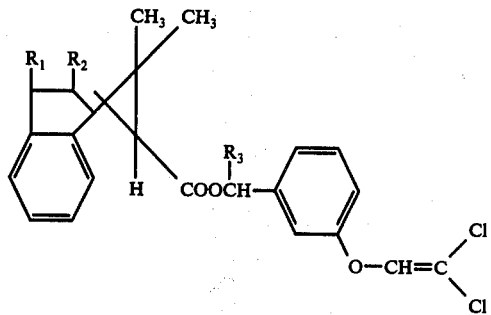

wherein each of
$R_1$ and $R_2$ represents a hydrogen atom or together represent a carbon to carbon bond, and
$R_3$ represents a hydrogen atom or a cyano group, process for their manufacture and a method of controlling pests, which comprises the use of these compounds.

6 Claims, No Drawings

PESTICIDAL BENZASPIRO CARBOXYLATES

The present invention provides 2,2-dimethyl-4,5-benzospiro(2,4)heptane- and 2,2-dimethyl-4,5-benzospiro(2,4)-hepta-4,6-diene-1-carboxylates, process for their manufacture, and a method of controlling pests, which comprises the use of these compounds.

The esters have the formula

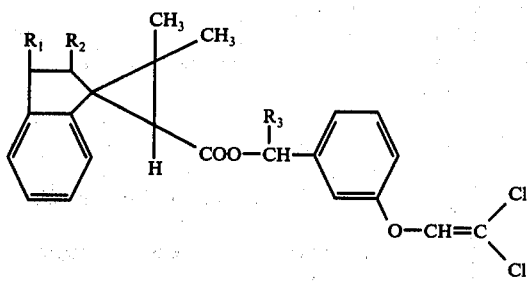

wherein
 each of $R_1$ and $R_2$ represents a hydrogen atom or together represent a carbon to carbon bond, and $R_3$ represents a hydrogen atom or a cyano group.

Particularly preferred compounds of account of their activity are those of the formula I, wherein each of $R_1$ and $R_2$ represents a hydrogen atom or together represent a carbon to carbon bond and $R_3$ represents a cyano group.

The compounds of the formula I are obtained by methods which are known per se by reacting for example (a) a compound of the formula

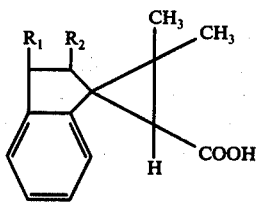

with a compound of the formula

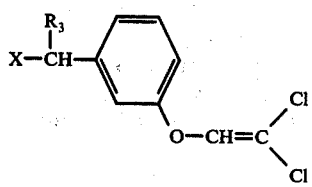

in the presence of a base;

(b) a compound of the formula

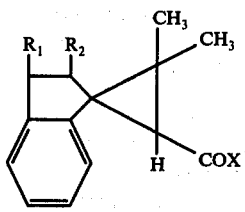

with a compound of the formula

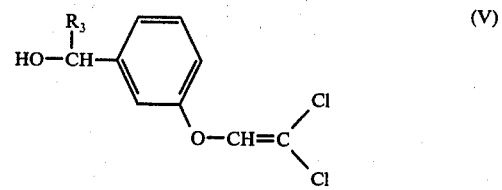

in the presence of a base; or (c) treating a compound of the formula II with a compound of the formula V in the presence of dicyclohexylcarbodiimide. In the formulae II to V, the symbols $R_1$ to $R_3$ are as defined in formula I and X represents a halogen atom, in particular a chlorine or bromine atom.

Processes (a) to (c) are carried out at a reaction temperature between −10° and +100° C, normally between 20° C and 80° C, at normal or elevated pressure, and preferably in a solvent or diluent which is inert to the reactants.

Suitable solvents or diluents for these reactions are for example: ether and ethereal compounds, such as diethyl ether, diisopropyl ether, dioxane, dimethoxyethane and tetrahydrofurane; ketones, such as acetone and methyl ethyl ketone; aliphatic, aromatic and halogenated hydrocarbons, in particular benzene, toluene, xylenes, chloroform, chlorobenzene and methylene chloride; dimethyl formamide, dimethyl sulphoxide and hexamethylphosphoric triamide.

Suitable bases for processes (a) and (b) are in particular tertiary amines, such as triethylamine, dimethyl aniline, pyridine, picolines and lutidines; hydroxides, oxides, carbonates and bicarbonates of alkali metals and alkaline earth metals; and alkali metal alcoholates, for example potassium tert. butylate and sodium methylate.

The derivatives of the formula II to V used as starting materials are known, see for example U.S. Pat. No. 3,823,177.

The compounds of the formula I are obtained in the form of different optically active isomers if starting materials which are not uniformly optically active are used in the process of manufacture. The various stable isomeric mixtures can be separated into the individual diastereoisomers for example by recrystallisation or by chromatographic methods of separation. The compounds of the formula I are to be understood as comprising both the individual optically active isomers and mixtures thereof.

The compounds of the formula I have a broad biocidal activity spectrum and can be used for controlling a variety of plant and animal pests, for example as acaracides, insecticides, ectoparasiticides, nematicides, fungicides, plant regulators or herbicides.

The active substances of the formula I are chiefly suitable for combating insects of the families: Acrididae, Blattidae, Gryllidae, Gryllotalpidae, Terrigoniidae, Cimicidae, Pyrrhocoridae, Reduviidae, Aphididae, Delphacidae, Diaphididae, Pseudococoidae, Chrysomilidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Galliphoridae, Trypetidae, and Pulicidae, and especially for controlling harmful insects in fruit, vegetable and cotton plantations (for example Spodoptera littoralis, Heliothis virescens and Myzus persicae) and house flies (for example *Musca domestica*).

The compounds of the formula I also act on representatives of the order Acarina, for example on mites and ticks of the families: Ixodidae, Argasidae, Tetranychidae and Dermanysidae.

The acaricidal or insecticidal action can be substantially broadened and adjusted to prevailing conditions by adding other insecticides or acaricides.

Examples of suitable additives are: nitrophenols and derivatives thereof; formamidines; ureas; pyrethroids; carbamates and chlorinated hydrocarbons.

The compounds of the formula I are particularly advantageously combined with substances which exert a synergistic or potentiating effect on pyrethroids. Examples of such compounds include piperonyl butoxide, propionyl ethers, propionyl carbamates and propionyl phosphinates, 2-(3,4-methylenedioxyphenoxy)-3,6,9-trioxandecane (Sesamex or Sesoxane), S,S,S-tributylphosphorotrithioates, 1,2-methylenedioxy-4-[2-(octylsulphonyl)-propyl]-benzene.

The compounds of formula I can be used as pure active substance or together with suitable carriers and/or additives. Suitable additives can be solid or liquid and correspond to the substances conventionally used in the art of formulation, such as natural or regenerated substances, solvents, dispersants, wetting agents, stickers, thickeners, binding agents and/or fertilizers.

The compositions of the present invention are obtained in known manner by intimately mixing and/or grinding active substances of formula I with the suitable carriers, with or without the addition of dispersants or solvents which are inert to the active substances.

The active substances can be in the form of and used in the following application forms:

Solids: dusts, tracking agents, granulates (coated granulates, impregnated granulates and homogranulates);
Liquids:
  a. concentrates of active substances which are dispersible in water: wettable powders, pastes, emulsions;
  b. solutions: The content of active substances in the formulations described above is between 0.1 and 95%, in which connection it is to be mentioned that when the compounds are applied from an aircraft or by other suitable means of application, higher concentrations can also be used.

The active substances of formula I can for example be formulated as follows:

Dust

The following substances are used to obtain (a) a 5% and (b) a 2% dust:
a. 5 parts of active compound, 95 parts of talcum.
b. 2 parts of active compound, 1 part of highly dispersed silicic acid, 97 parts of talcum
The active substances are mixed with the carriers and ground.

Granulate

For the preparation of a 5% granulate the following ingredients are used:
5 parts of active substance,
0.25 part of epichlorohydrine,
0.25 part of cetyl polyglycol ether,
3.50 parts of polyethylene glycol,
91 parts of kaolin (particle size 0.3 to 0.8 mm).

The active compound is mixed with epichlorohydrin and dissolved in 6 parts of acetone, then polyethylene glycol and cetyl polyglycol ether are added. The resultant solution is sprayed onto kaolin and the acetone is subsequently evaporated in vacuo.

Wettable powder

The following ingredients are used to prepare (a) a 40%, (b) and (c) a 25% and (d) a 10% wettable powder:
(a)
  40 parts of active substance,
  5 parts of sodium lignin sulphonate,
  1 part of sodium dibutyl-naphthalene sulphonate,
  54 parts of silicic acid;
(b)
  25 parts of active substance,
  4.5 parts of calcium lignin sulphonate,
  1.9 parts of Champagne-chalk/hydroxyethylcellulose mixture (1:1),
  1.5 parts of sodium dibutyl-naphthalenesulphonate,
  19.5 parts of silicic acid,
  19.5 parts of Champagne-chalk,
  28.1 parts of kaolin;
(c)
  25 parts of active substance,
  2.5 parts of isooctylphenoxy-polyethylene-ethanol,
  1.7 parts of Champagne-chalk/hydroxyethylcellulose mixture (1:1),
  8.3 parts of sodium aluminium silicate,
  16.5 parts of kieselguhr,
  46 parts of kaolin;
(d)
  10 parts of active substance,
  3 parts of a mixture of sodium salts of saturated fatty alcohol sulphonates,
  5 parts of naphthalenesulphonic acid/formaldehyde condensate,
  82 parts of kaolin.

The active compounds are intimately mixed with the additives in suitable mixers and ground in appropriate mills and rollers to yield wettable powders, which can be diluted with water to give suspensions of the required concentration.

Emulsifiable concentrates

The following substances are used to obtain (a) a 10%, (b) a 25%, (c) a 50% emulsifiable concentrate:
(a)
  10 parts of active substance,
  3.4 parts of epoxidised vegetable oil,
  3.4 parts of a combination emulsifier, composed of fatty alcohol polyglycol ether and calcium alkylarylsulphonate,
  40 parts of dimethyl formamide,
  43.2 parts of xylene;
(b)
  25 parts of active substance,
  2.5 parts of epoxidised vegetable oil,
  10 parts of an alkylarylsulphonate/fatty alcohol polyglycol ether mixture,
  5 parts of dimethyl formamide
  57.5 parts of xylene;
(c)
  50 parts of active substance,
  4.2 parts of tributylphenol polyglycol ether,
  8.5 parts of calcium dodecylbenzenesulfonate,
  20 parts of cyclohexanone,
  20 parts of xylene.

Emulsions of any required concentration can be prepared by diluting the above described concentrates with water.

Spray

The following ingredients are used to obtain (a) a 5% and (b) a 95% spray:

(a)
- 5 parts of active compound,
- 1 part of epichlorohydrin,
- 94 parts of ligroin (boiling range 160–190° C);

(b)
- 95 parts of active compound,
- 5 parts of epichlorohydrin.

The following Examples will serve to illustrate the invention in more detail.

EXAMPLE 1

Preparation of 3-(2,2-dichlorovinyloxy)-benzyl-2',2'-dimethyl-4',5'-benzospiro(2',4')hepta-4',6'-diene-1'-carboxylate To a solution of 5.35 g (0.025 mole) of 2,2-dimethyl-4,5-benzospiro(2,4) hepta-4,6-diene-1-carboxylic acid in 50 ml of hexamethylphosphoric triamide are added 4.1 g (0.03 mole) of potassium carbonate. Then 7.05 g (0.025 mole) of 3-(2,2-dichlorovinyloxy)-benzyl-bromide are added dropwise and the reaction mixture is stirred for 16 hours at room temperature. The reaction mixture is worked up by pouring it onto water and extracting with ether. The ether phase is washed twice with water and twice with a saturated solution of sodium chloride, then dried over sodium sulphate. The solvent is thereafter distilled off and the oily residue is purified by column chromatography (silica gel/ether:hexane = 1:4) to yield the product of the formula

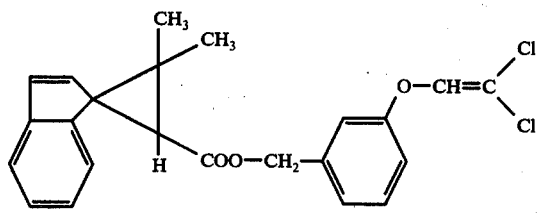

as a diastereoisomer mixture: $n_D^{20} = 1.5971$.

The following compounds of the formula

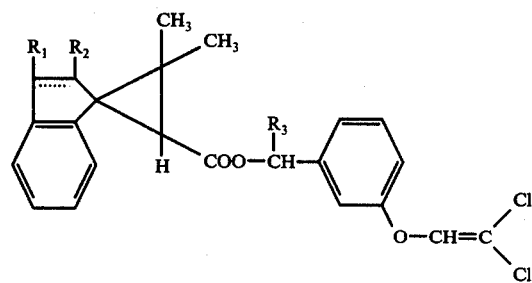

are also obtained in analogous manner.

| $R_1$ | $R_2$ | $R_3$ | Physical data |
|---|---|---|---|
| | C-C-bond | CN | $n_D^{20}$: 1,5856 |
| H | H | H | $n_D^{20}$: 1,5829 |
| H | H | CN | $n_D^{20}$: 1,5683 |

EXAMPLE 2

Stomach poison action on *Spodoptera littoralis, Heliothis virescens* H and *Leptinotarsa decemlineata*

Cotton plants and potato plants were sprayed with a 0.05% aqueous emulsion of active substance (obtained from a 10% emulsifiable concentrate). After the spray coating had dried, the cotton plants were populated with *Spodoptera littoralis* and *Heliothis virescens* larvae in the $L_3$ stage and the potato plants with larvae of the potato beetle (*Leptinotarsa decemlineata* larvae in the $L_3$ stage). The test was carried out at 24° C and 60% relative humidity.

In this test, the compounds of Example 1 exhibited a good insecticidal stomach poison action on the larvae of Spodoptera littoralis, Heliothis virescens and Leptinotarsa decemlineata.

EXAMPLE 3

Action of Chilo suppressalis

Six rice plants of the variety Caloro were transplanted into each of a number of plastic pots having a diameter of 17 cm at the top, and reared to a height of approx. 60 cm. Infestation with larvae of Chilo suppressalis ($L_1$ stage; 3 to 4 mm in length) took place 2 days after the active substance had been added to the paddy water in granulate form (rate of application; 8 kg of active substance/hectare). Evaluation of the insecticidal action took place 10 days after addition of the granulate. The compounds of formula I acted in this test on *Chilo suppressalis*.

We claim:

1. A compound of the formula

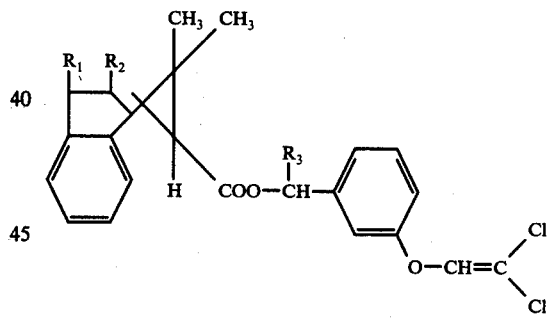

wherein each of $R_1$ and $R_2$ represents a hydrogen atom or together represent a carbon to carbon bond, and $R_3$ represents a hydrogen atom or a cyano group.

2. A compound according to claim 1, wherein each of $R_1$ and $R_2$ represents a hydrogen atom or together represent a carbon to carbon bond, and $R_3$ represents a cyano group.

3. The compound according to claim 2 of the formula

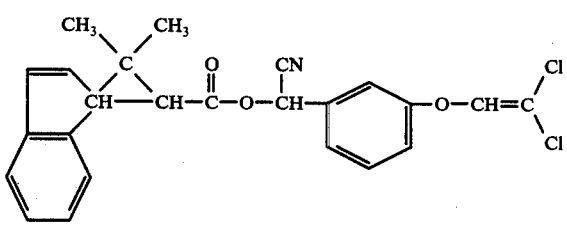

4. The compound according to claim 2 of the formula

[Chemical structure diagram showing a cyclopropane carboxylate ester with ethyl-substituted phenyl group and dichlorovinyl phenoxy cyanomethyl ester]

5. An insecticidal and acaricidal composition comprising an insecticidally and acaricidally effective amount of a compound according to claim 1, together with a suitable carrier therefor.

6. A method for combatting insects and acarids comprising applying to the locus thereof an insecticidally and acaricidally effective amount of a compound according to claim 1.

* * * * *